(12) United States Patent
Brewer (10) Patent No.: US 7,384,599 B2
(45) Date of Patent: Jun. 10, 2008

(54) APPARATUS FOR DRUG TESTING

(76) Inventor: Randy Brewer, 407 E. 4th, Kingman, KS (US) 67068

( * ) Notice: Subject to any disclaimer, the term of this patent is extended or adjusted under 35 U.S.C. 154(b) by 179 days.

(21) Appl. No.: 10/354,453

(22) Filed: Jan. 30, 2003

(65) Prior Publication Data

US 2004/0151624 A1   Aug. 5, 2004

(51) Int. Cl.
G01N 33/48 (2006.01)
(52) U.S. Cl. .............. 422/61; 422/58; 436/901
(58) Field of Classification Search ........... 422/55–61; 436/164, 166, 816, 901
See application file for complete search history.

(56) References Cited

U.S. PATENT DOCUMENTS

| | | | |
|---|---|---|---|
| 2,533,089 A | 12/1950 | Brewer et al. | |
| 2,874,091 A | 2/1959 | Fisk | |
| 3,036,894 A * | 5/1962 | Forestiere | 436/165 |
| 3,055,808 A | 9/1962 | Henderson | |
| 3,912,596 A | 10/1975 | Haque | |
| 3,985,264 A | 10/1976 | Shaw et al. | |
| 4,042,463 A | 8/1977 | Haque | |
| 4,690,801 A * | 9/1987 | Anderson | 422/61 |
| 4,707,450 A * | 11/1987 | Nason | 600/572 |
| 4,752,448 A | 6/1988 | Wells et al. | |
| 4,769,333 A * | 9/1988 | Dole et al. | 422/58 |
| 4,801,548 A | 1/1989 | Takakura et al. | |
| 4,992,296 A | 2/1991 | Gibson | |
| 5,119,830 A * | 6/1992 | Davis | 600/584 |
| 5,141,875 A | 8/1992 | Kelton et al. | |
| 5,229,297 A * | 7/1993 | Schnipelsky et al. | 436/94 |
| 5,457,054 A | 10/1995 | Geisinger et al. | |
| 5,496,520 A | 3/1996 | Kelton et al. | |
| 5,611,782 A * | 3/1997 | Haedt | 604/198 |
| 6,108,588 A | 8/2000 | McGrady | |
| 6,669,908 B2 * | 12/2003 | Weyker et al. | 422/58 |

* cited by examiner

*Primary Examiner*—Lyle A. Alexander
(74) *Attorney, Agent, or Firm*—Robert O. Blinn (57) ABSTRACT

An apparatus for testing for the presence of a drug is provided. The apparatus includes a first drug testing reagent, a first ampule, a vessel that contains the first ampule, and a fracturing means. The first drug testing reagent contains a controlled substance detecting chemical reagent. The vessel serves as a mixing chamber for mixing the reagents with the test subject fluid. Further, the vessel may include a transparent wall through which changes in coloration of mixtures of test subject fluids and reagents may be viewed. The vessel may also comprise a test subject fluid injection port to allow for the injection of a test subject fluid into the vessel. The vessel may also contain means for fracturing the ampule without damaging or opening the vessel. A method for conducting a drug test is also provided.

2 Claims, 7 Drawing Sheets

APPARATUS FOR DRUG TESTING

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to drug testing. More particularly, this invention relates to color change indicia chemical reagent drug testing, and to apparatus and method steps for facilitating color change indicia chemical reagent drug testing.

Conducting tests for the presence or absence of drugs is known. One method of testing for the presence of a drug is to mix a reagent with the substance to be tested, which indicates the presence of a drug by a color change. Commonly known chemical reagents for color change indicia testing for the presence or absence of controlled substance drugs include Meyer's reagent, Marquis reagent, Nitric acid reagents, Cobalt Thiocyanate reagent, Dille-Koppanyi reagent, Mandeline reagent, Mecke's modified reagent, and Diazepam/Valium reagent. Classes of controlled substance drugs which are detectable through reagent color indicia testing include barbiturates, amphetamines, opiates, and synthetic opiates.

In order to test for the presence or absence of controlled substance drugs, a reagent, for example liquid nitric acid, is commonly held in an unsealed container. Thereafter, a test subject fluid, for example a fluid suspected of including the opiate Demerol, is introduced and mixed with the nitric acid fluid within the open-ended container. A change in coloration of the solution represents a positive result, indicating the presence of an opiate. The absence of any change in coloration indicates the absence of opiates within the test subject fluid.

However, the performance of such chemical reagent drugs tests suffer from a number of drawbacks and deficiencies. For instance, the test described above typically requires one or more measuring steps and the manipulation of various vials, which can be time consuming and inconvenient. Moreover, the aforementioned technique may result in mis-measurements, inaccuracies, and spillage of liquids, which may compromise the reliability of the test results. Furthermore, the vials and vessels used to perform such drug tests commonly have no capacity for preserving the results of a test for future observation.

Accordingly, there exists a need for a convenient apparatus and method for testing for the presence of a drug that substantially reduces mis-measurements, inaccuracies and the spillage of liquids while providing for the preservation of the test result. The present invention fills these needs as well as other needs.

BRIEF SUMMARY OF THE INVENTION

In order to overcome the above stated problems and limitations there is provided a drug testing apparatus that is convenient, efficient and allows for the preservation of the test result.

In general, the apparatus may include a first drug testing reagent, a first ampule, a vessel and a fracturing means. The first drug testing reagent comprises a controlled substance detecting or indicating chemical reagent such as, but not limited to, Meyer's reagent, Marquis reagent, Nitric acid reagents, Cobalt Thiocyanate reagent, Dille Koppanyi reagent, Mandeline reagent, Mecke's modified reagent, or Diazepam/Valium reagent. The first reagent may be hermetically sealed within the first ampule. The first ampule includes a frangible wall and is contained within the vessel. In particular, the first ampule may be formed of a tubular shaped thin glass wall having hermetically closed ends, such ends preferably comprising crimped heat fusion closures. Where a particular drug test requires multiple reagents, multiple frangible ampules containing different reagents may be provided within the vessel.

The first ampule contains a drug testing reagents that is contained within the vessel. The vessel serves as a mixing chamber for mixing the reagents with the test subject fluid. The vessel may include a transparent wall through which changes in coloration of mixtures of test subject fluids and reagents may be viewed. The vessel also may comprise a test subject fluid injection port, such as, but not limited to, those common to hypodermic injection vials. The test subject injection port may include a pierceable elastomeric cannula receiving membrane that closes or covers the port so that the test subject fluid may no escape into an external environment. The vessel may also contain means for fracturing the ampules without damaging or re-opening the vessel.

The ampule fracturing means may comprise an inwardly flexible wall of the vessel, such wall being inwardly flexible to the extent that an inner surface of such wall may impinge upon the one or more ampules contained within the vessel. The fracturing means fractures the ampule causing as release of the reagent within the vessel. Further, the ampule fracturing means may comprise a positioning of the test subject injection port to underlie or overlie an ampule within the vessel, allowing a cannula extending through such port to impinge upon and fracture the ampule. Furthermore, the ampule fracturing means may comprise a moveable member, for example, a steel ball, within the vessel, such moveable member being capable of percussively striking and fracturing the ampule.

Additionally, the interior surface of the vessel may comprise ampule holding brackets for fixedly positioning the ampules within the second vessel. Further, an absorbent, such as, but not limited to, a fibrous pad may be contained within the vessel for absorbing mixtures of test subject fluids and reagents after testing and use. A splash guard wall may also be disposed within the vessel and between the absorbent and the ampules to prevent the absorbent from receiving and absorbing testing subject fluids or reagents prior to completion of a drug test.

A method for conducting a drug test is also within the scope of the present invention. Assuming, for example, that an operator is in possession of a test subject fluid which is suspected of including an opiate, the operator selects a drug test vessel containing a nitric acid filled ampule. The test subject fluid is preferably contained within a hypodermic syringe. Such operator uses the cannula on the syringe to pierce the elastomeric membrane covering the chamber's test subject fluid injection port. The hypodermic syringe is then operated to inject the test subject fluid into the interior space of the vessel. Thereafter, the operator manually presses inwardly upon the vessel's flexible wall, causing the wall to impinge upon and fracture the nitric acid filled ampule contained therein causing the nitric acid to spill into the interior space of the vessel, and allowing mixing of the nitric acid and the test subject fluid. The operator may then view the interior space of the vessel through such vessel's transparent wall, observing any change in coloration of the mixture. In the event a coloration change is observed, a positive test result is noted, indicating the presence of an opiate within the test subject fluid. The vessel may then be tilted so that the lower surface of the vessel slopes downwardly toward the absorbent to allow the absorbent to receive and retain the mixed fluids.

A procedure substantially identical to that described above may be performed where an operator is in possession of a controlled substance drug such as Demerol, where the operator has need of disposing of such drug, and where the operator has further need of confirming and verifying to others that such drug has been properly disposed of or wasted as opposed to having been misappropriated. In such circumstance, the present invention serves as a convenient chamber for controlled substance drug wastage, the above described method serving as a means for verifying that a drug wastage event has properly occurred to prevent drug misappropriation.

Accordingly, the present invention provides a drug testing or drug wastage vessel or chamber which is capable of facilitating drug testing or of drug wastage verification through the performance of a single exterior fluid handling step, that step being fluid injection into the chamber where all other fluid handling steps, including fluid storage, occurs within the interior of such chamber. The present invention also provides a drug testing or drug wastage chamber including or containing a transparent wall, a fluid injection port, frangible reagent vials or ampules, and means for fracturing contained ampules without opening the chamber. Moreover, the present invention to provide a method for using the apparatus described above.

Additional objects, advantages and novel features of the present invention will be set forth in part in the description which follows, and will in part become apparent to those in the practice of the invention, when considered with the attached figures.

BRIEF DESCRIPTION OF THE SEVERAL VIEWS OF THE DRAWINGS

The accompanying drawings form a part of the this specification and is to be read in conjunction therewith, wherein like reference numerals are employed to indicate like parts in the various views, and wherein.

DETAILED DESCRIPTION OF THE INVENTION

Figure 1:
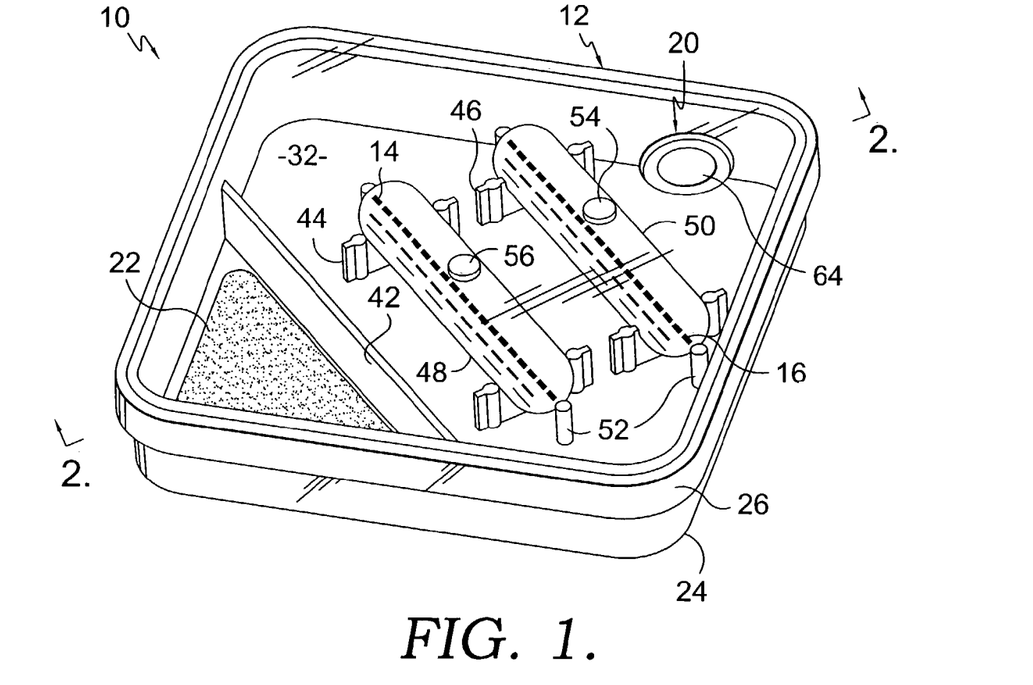
FIG. 1 is a perspective view of the apparatus constructed in accordance with the present invention.

Referring now to the drawings in detail, and initially to FIG. 1, reference numeral 10 generally designates the drug testing apparatus constructed in accordance with a first embodiment of the present invention. With additional reference to FIG. 7, apparatus 10 includes a hermetically sealed vessel 12 having reagents 14, 16 contained therein that are capable of indicating or verifying the presence of a drug when combined with a test subject fluid 18. Test subject fluid 18 may be inserted into vessel 12 through an injection port 20, which prevents any fluid contained within vessel 12 from being transferred to into an external environment. Apparatus 10 may also have an absorbent material 22 contained therein to absorb reagents 14, 16 and test subject fluid 18 after the test has been completed.

Figure 2:
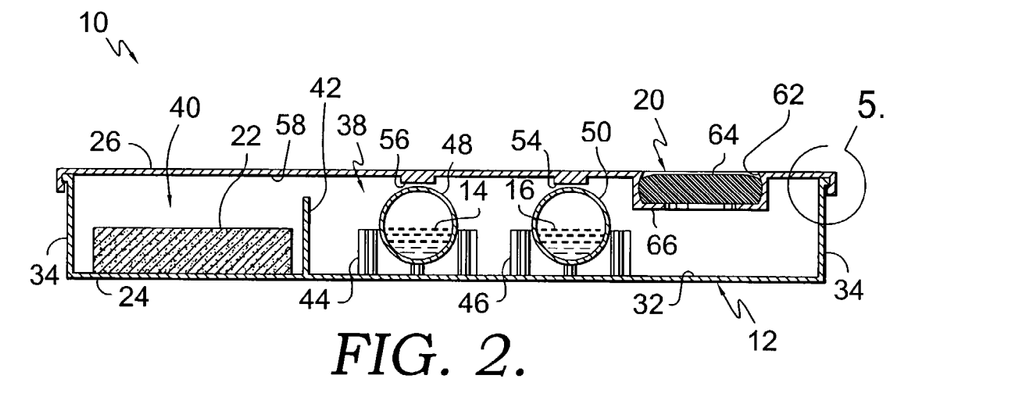
FIG. 2 is a cross-sectional view taken along line 2-2 in FIG. 1.
Figure 3:
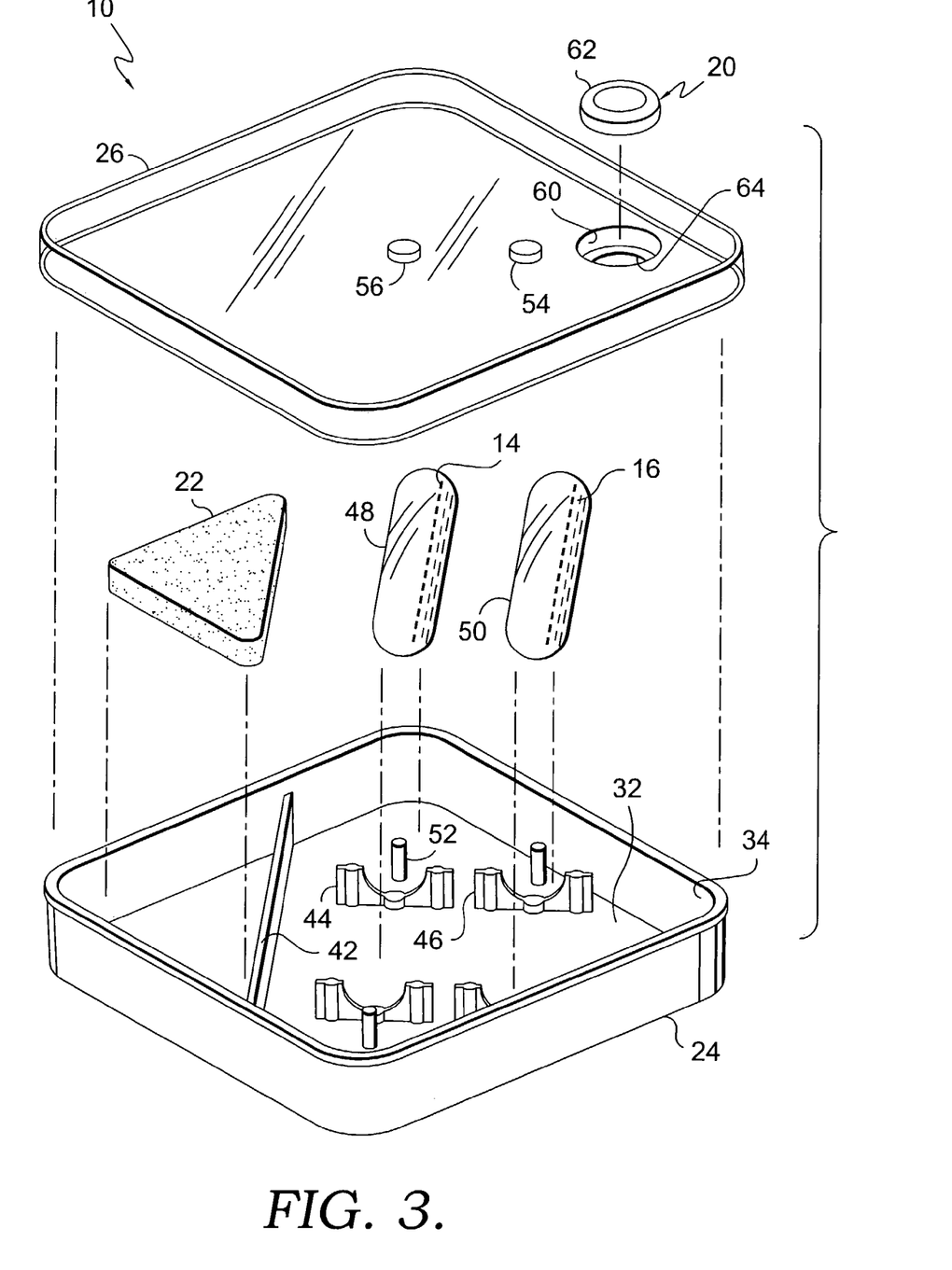
FIG. 3 is an exploded view of the apparatus shown in FIG. 1.
Figure 4:
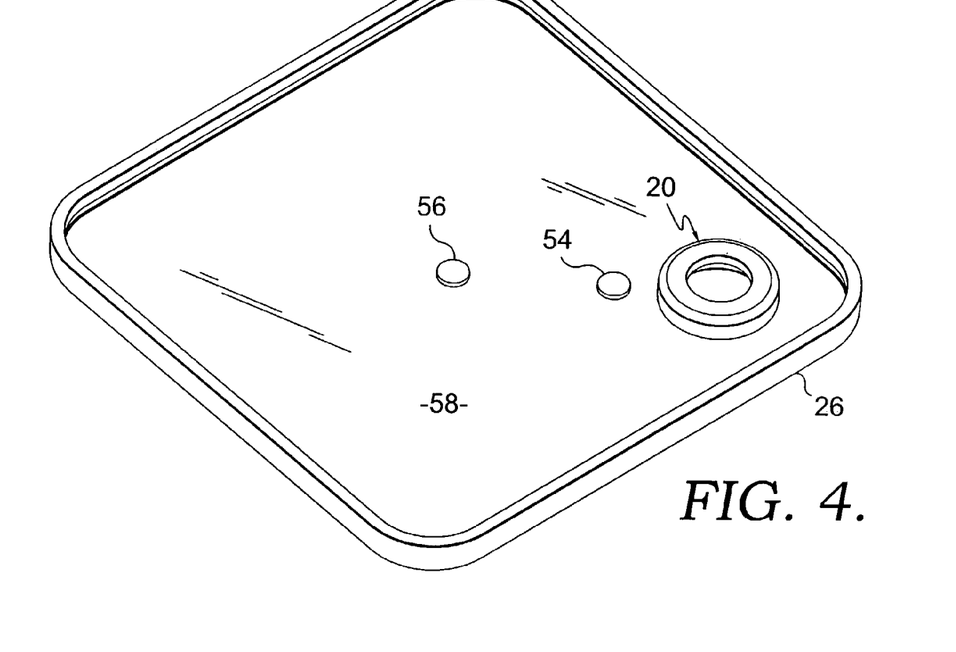
FIG. 4 is a perspective view of the inner surface of a lid that forms a part of the apparatus shown in FIG. 1.
Figure 5:
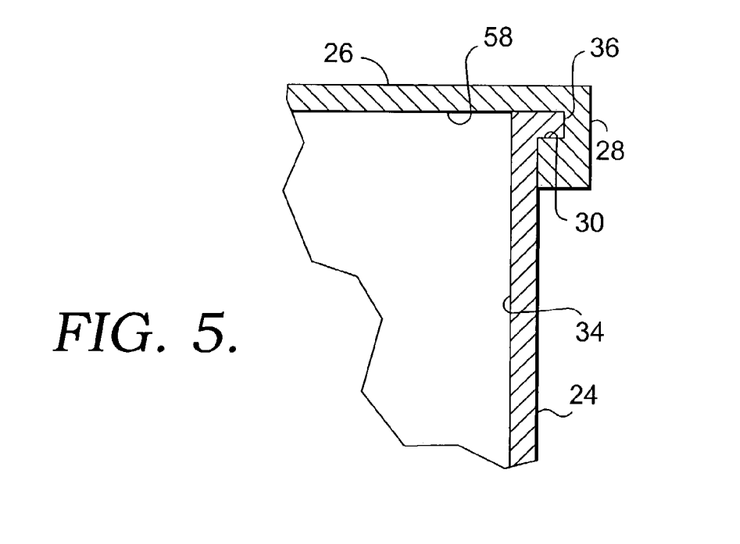
FIG. 5 is an enlarged view of the area designated by reference numeral "5" in FIG. 2 showing the connection between the lid and bowl of the apparatus.
Figure 6:
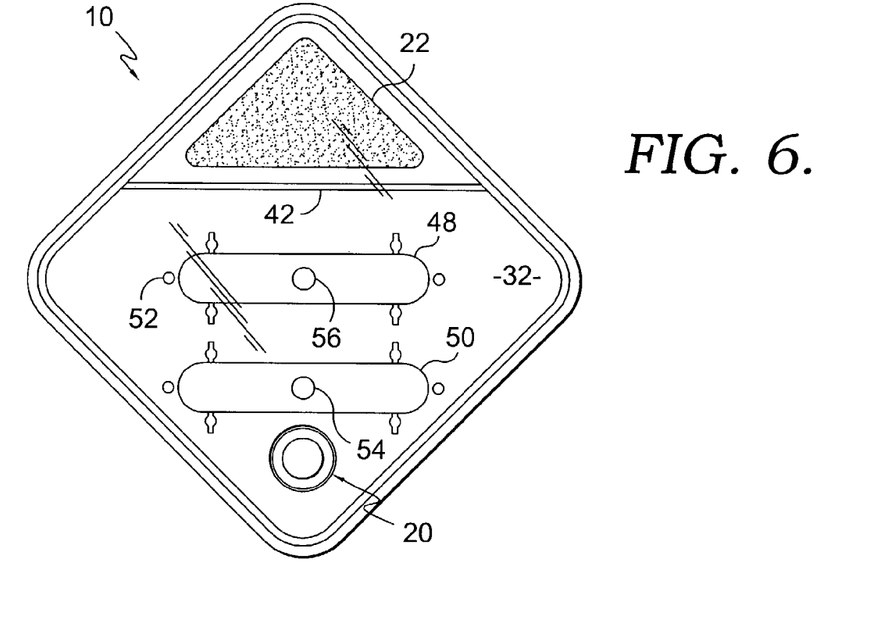
FIG. 6 is a top view of the apparatus shown in FIG. 1.

As best seen in FIGS. 1-3, vessel 12 may include a lower "clam shell" bowl 24 and an upper "clam shell" lid 26. With additional reference to FIG. 5, the periphery of lid 26 may include a downwardly extending flange 28 having an inwardly extending lock ridge 30. Further, bowl 24 may have a lower surface 32 with an upstanding wall 34 that extends upwardly from the periphery of lower surface 32. The upper edge of upstanding wall 34 includes an outwardly extending lock ridge 36 that is selectively engagable with flange 28 and inwardly extending lock ridge 30. Upon compressively fitting lid 26 over bowl 24, ridges 30, 36 engage with each other so that lid 26 and bowl 24 are locked and sealed with one another. Specifically, the connection between lid 26 and bowl 24 hermetically seals the interior space defined by lid 26 and bowl 24 so that fluid contained within vessel 12 is unable to pass between lid 26 and bowl 24. Preferably, interlocking ridges 30, 36 engage each other with a strength sufficient to prevent manual disassembly. Furthermore, vessel 12 is preferably a generally rectangularly shaped, but it will be understood that vessel 12 may also be shaped in accordance with numerous other common geometric shapes. In addition, it is also within the scope of the present invention to provide a vessel that is a one-piece structure.

As best seen in FIG. 2, vessel 12 may include an ampule chamber 38 and an absorbing chamber 40, each being defined by a splash guard wall 42, upstanding wall 34 and lid 26. In particular, the vertical height of splash guard wall 42 is less than the height of upstanding wall 34 of the vessel 12 so that test subject fluid 18 and reagents 14, 16 may flow from ampule chamber 38 into absorption chamber 40.

As best seen in FIGS. 1-3, lower surface 32 of bowl 24 include a pair of brackets 44, 46 that may be fixedly attached to lower surface 32 or integrally formed therewith. Further, brackets 44, 46 are adapted to cradle frangible glass ampules 48, 50 and hold them in position. It will be understood and appreciated that ampules 48, 50 may be a vessel or another type of enclosed container. Further, ampules 48, 50 may be cradled within brackets 44, 46 so that they are positioned off of lower surface 32 of bowl 24 by approximately one-eighth inch. However, it is also within the scope of the present invention to position ampules at other distances from lower surface 32. Further, a pair of end pieces 52 are positioned on opposite sides of ampules 48, 50 to prevent them from moving or sliding relative to each of their longitudinal axis. Frangible ampules 48, 50 necessarily contain drug testing reagents that may fill the entire ampule, or just a portion thereof depending on the drug being tested. Where a particular drug test to be performed by vessel 12 requires use of only one reagent, a single ampule may be used and positioned in either of ampule brackets 44, 46. In addition, the present invention may also include the use of more than two reagents depending on the drug to be tested, which of course may also include the addition of additional ampules within vessel 12. Moreover, it is also within the scope of the present invention to eliminate the use of ampules 48, 50 to allow one or more reagents to flow freely within vessel 12 prior to introducing test subject fluid 18. If no ampules are used in conjunction with the reagents, then vessel 12 may be formed of a material that will not deteriorate under prolonged exposure to the reagents used in the present invention.

As best seen in FIGS. 1-4, lid 26 may have ampule fracturing lugs or protrusions 54, 56 fixedly attached, or integrally formed, to an inner surface 58 of lid 26. In particular, protrusions 54, 56 may be positioned in such a way that they overlie or aligned with ampules 48, 50. It will be understood and appreciated that the number of protrusions included in the present invention may correspond to the number of ampules contained within vessel 12. It will of course understood that protrusions 54, 56 may be in any size or shape that will operate to break ampules 48, 50. Further, lid 26 may be formed of a flexible plastic that allows lid 26 to be manually flexed from a normal position, depicted in FIG. 1, to an inwardly flexed position. When lid 26 is in a flexed position, protrusions 54, 56 impinge downwardly upon, and respectively fracture, ampules 48, 50, allowing reagents contained therein to spill into interior spaces of vessel 12. It will also be understood that other means may be utilized in place of, or in addition to, protrusions 54, 56 to break ampules 48, 50. Further, ampules 48, 40 may also be fractured by a positioning of test subject injection port 20 to underlie or overlie ampules 48, 50 within vessel 12, allowing cannula 60 extending through injection port 20 to impinge upon and fracture ampules 48, 50. Furthermore, ampules 48, 50 may also be fractured by a moveable member, for example, a steel ball, within vessel 12, such moveable member being capable of percussively striking and fracturing either or both of ampules 48, 50.

Figure 7:
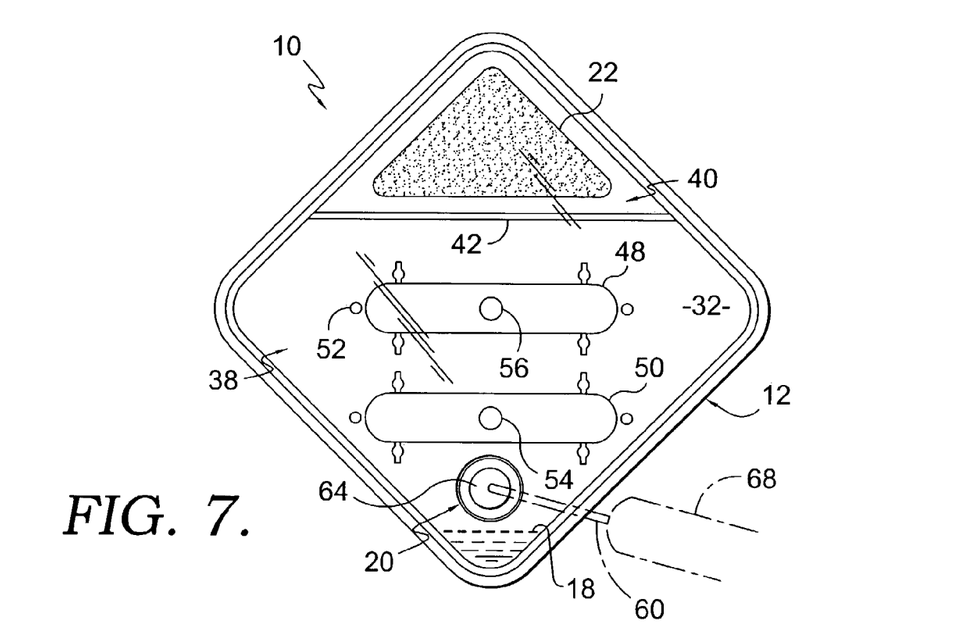
FIG. 7 is a top view similar to FIG. 6 showing completion of a test subject fluid injection step.

As best seen in FIGS. 1 and 7, lid 12 may also include test subject fluid injecting port 20 that is adapted to allow test subject fluid 18 into vessel 12. As best seen in FIG. 3, injection port 20 is positioned within an aperture 62 formed in lid 26, and may include a cannula receiving elastomeric membrane 64 that allows for the passage of fluid from an external environment to the inside of vessel 12. In particular, as best seen in FIGS. 2 and 3, elastomeric membrane 64 is positioned within aperture 62 and is seated on an inwardly extending ridge 66. As best seen in FIG. 7, it will be understood that a cannula 60 or similar device may be used to penetrate elastomeric membrane 64 and allow for the insertion of test subject fluid 18 into vessel 12. Elastomeric membrane 64 prohibits test subject fluid 18 from moving back into the external environment from vessel 12 through injection port 20.

As best seen in FIGS. 1 and 2, a fibrous absorbent material 22, such as a sponge, may be contained within absorption chamber 40 within vessel 12. Thus, pad 22 may be partitioned from ampules 48, 50 by splash guarding wall 42 to prevent the absorbent from receiving and absorbing testing subject fluids or reagents prior to completion of a drug test.

As best seen in FIG. 1, at least a portion of vessel 12 may be transparent or otherwise able to allow for viewing of any color changes of fluids contained therein. In particular, lid 26 may be formed of a transparent material. Further, both lid 26 and bowl 24 may be formed of a transparent material such as, but not limited to, plastic or other types of polymeric material. In the case where the entire vessel 12 is formed of a transparent material, a white adhesive label, not depicted, may be affixed to the outer surface of vessel 12 to provide a white background which aids in viewing of coloration changes in test subject fluid and reagents, and as media for writing or printing reagent used in the drug test, the drug believed to be inserted into vessel 12, the resulting color of the reagent and drug mixture, the name of the individual witnessing the insertion of the test subject fluid into vessel 12, and other information. However, it will be understood that vessel 12 may also be formed of an opaque material that may not allow for the viewing of the contents contained within vessel 12. In this case, other means for determining the results of the drug test may be used with the present invention such as, but not limited to, spectrometry, electroanalysis, and other types of tests that convey the test results to the user.

The types of drug testing reagents 14, 16 that may be used in the present invention include, but are not limited to, Meyer's reagent, Marquis reagent, Nitric acid reagents, Cobalt Thiocyanate reagent, Dille Koppanyi reagent, Mandeline reagent, Mecke's modified reagent, or Diazepam/Valium reagent. It will be understood that either liquid or dry reagents may be used with the present invention. The use of other types of drug testing regents are also within the scope of the present invention.

Figure 12:
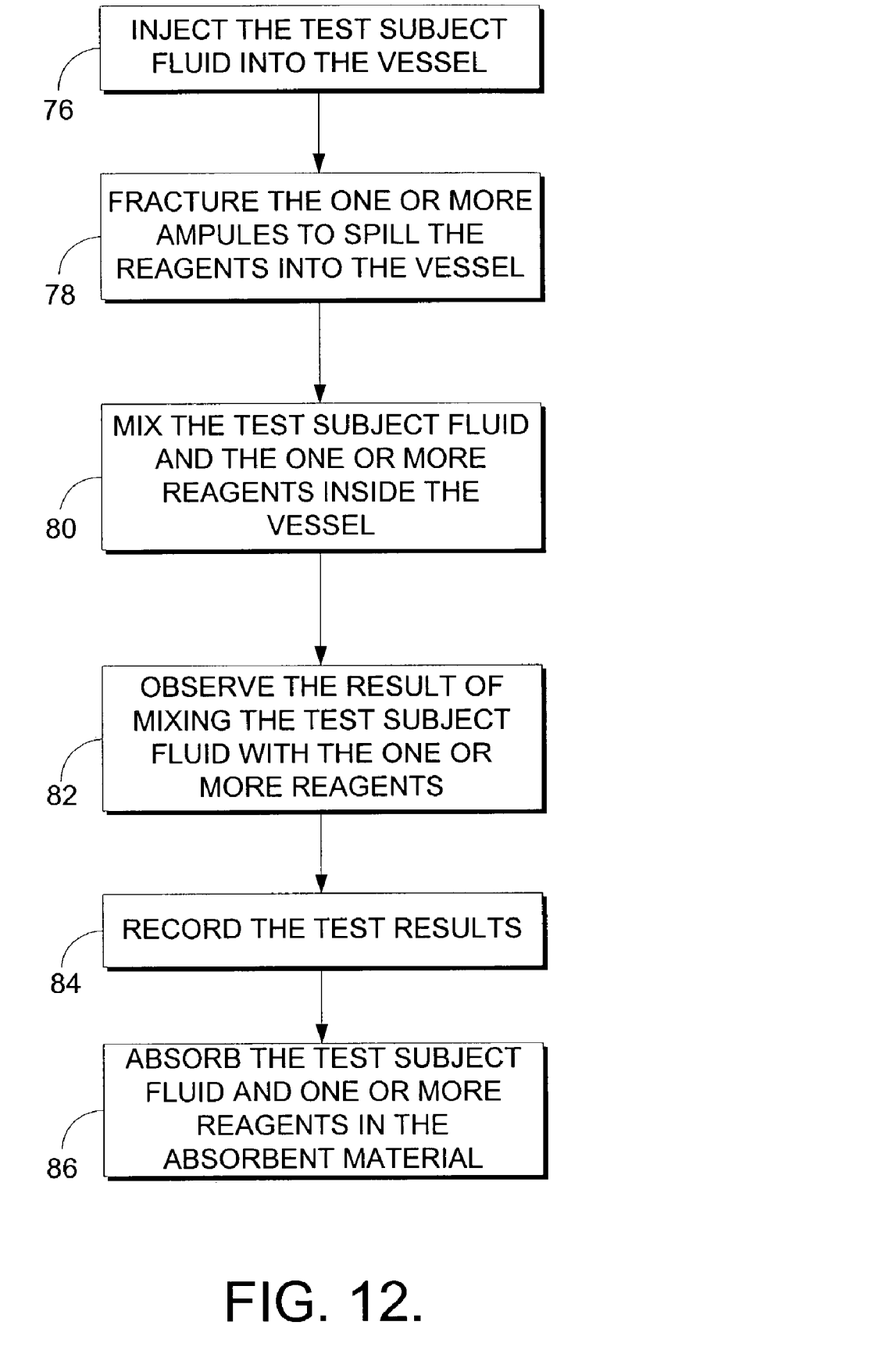
FIG. 12 is a flow chart of a method for testing drugs according to the present invention.

In performing the method of the present invention, test subject fluid 18 is contained within a hypodermic syringe 68 having cannula 60 or other type of fluid transfer device that is capable of transferring test subject fluid through injection port 20. The point of cannula 60 is placed on the surface of elastomeric membrane 64, and cannula 60 is driven through membrane 64 to extend into the interior space of vessel 12. As best seen in FIG. 12, the plunger of such hypodermic syringe is then operated to inject test subject fluid 18 through injection port 20, into the interior space of vessel 12 in step 76. When cannula 60 is withdrawn from injection port 20, the elastic character of membrane 64 closes the injection aperture to reseal vessel 12 and prevent test subject fluid 18 from being transferred out of vessel 12.

Next, as best seen in FIG. 7, vessel 12 may be vertically oriented so that test subject fluid pool 18 flows to the lower corner of vessel 12, which may be ampule chamber 38. However, it is also within the scope of the present invention to orient vessel 12 in a generally horizontal plane or other orientation so that test subject fluid 18 is distributed on all, or a part of lower surface 32 of bowl 24.

Figure 8:
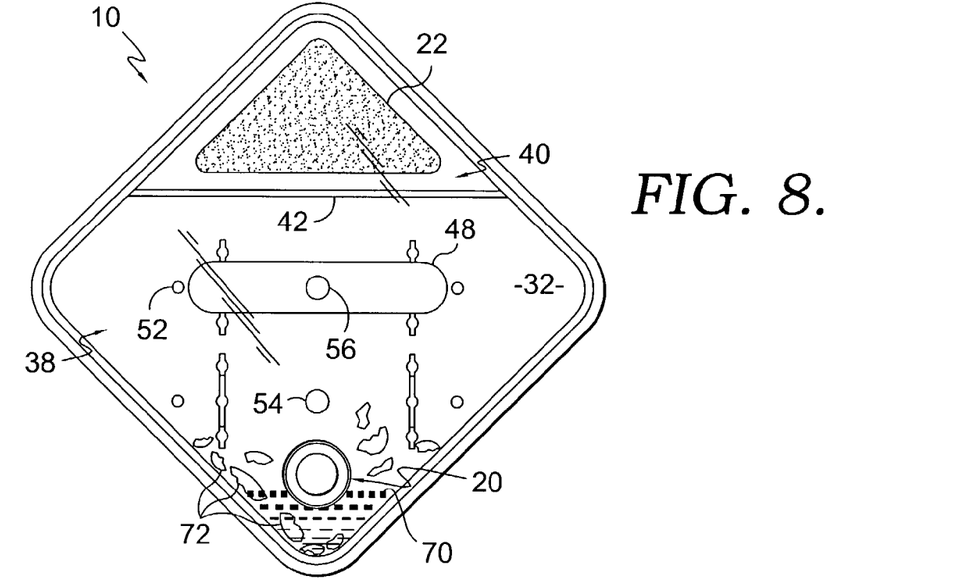
FIG. 8 is a top view similar to FIG. 7 and sequentially shows completion of a first ampule fracturing step.

As best seen in FIGS. 8 and 12, lid 26 is manually pressed inwardly so that protrusion 54 impinges upon frangible ampule 50 thereby fracturing frangible ampule 50 at step 78. Fracturing ampule 50 causes reagent 16 contained therein to spill out into ampule chamber 38 allowing reagent 16 and test subject fluid 18 to form pool 70. Due to the fracturing of ampule 50, there may also be shards 72 included within pool 70 or located on lower surface 32. The sealed connection between lid 26 and bowl 24 keeps pool 70 retained within vessel 12. However, it will be understood that this step may not be necessary of ampule 50 is not used to contain reagent 16.

Figure 9:
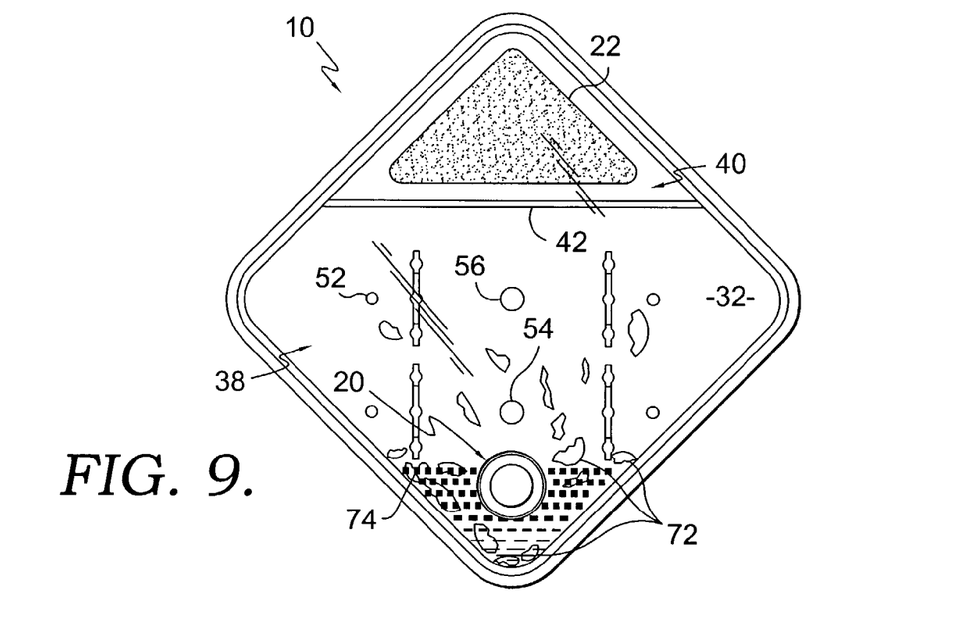
FIG. 9 is a top view similar to FIG. 8 and sequentially shows completion of a second ampule fracturing step.

Thereafter, as best seen in FIGS. 9 and 12, and assuming that the drug test being performed requires two separate reagents included within separate ampules, lid 26 may once again be pressed inwardly causing protrusion 56 to fracture ampule 48 thereby causing it to spill reagent 14 into the interior of vessel 12 also represented by step 78. Breaking ampule 48 results in the mixing of test subject fluid 18, reagent 14 and reagent 16 thereby forming pool 74 at step 80. Fluid pool 74 not only contains test subject fluid 18, reagent 14, reagent 16, but also may contain shards 72 from ampules 48, 50. However, it will be understood that this particular step may not be necessary of ampule 48 is not used to contain reagent 14. In any case, the operator, or some other user of vessel 12 observes the color of fluid pool 74 at step 82, noting any positive or negative drug test results on the white adhesive label at step 84. In addition, it will be understood that it is also within the scope of the present invention to break ampules 48, 50 at the same time.

Figure 10:
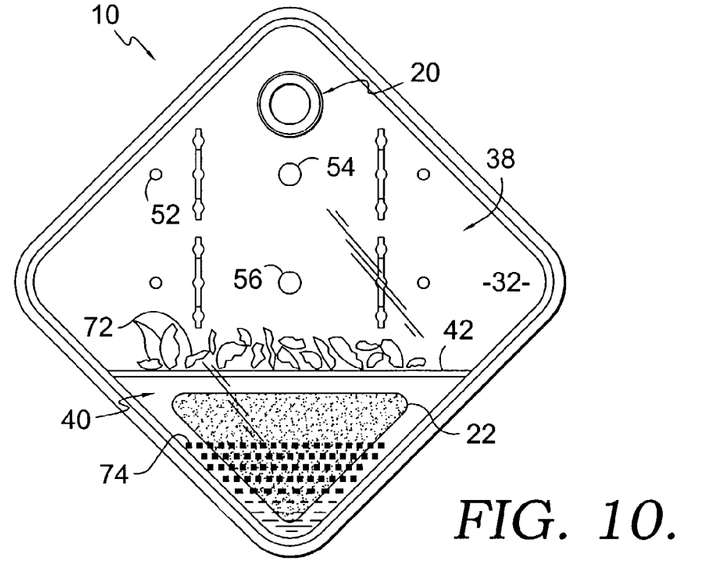
FIG. 10 is a top view similar to FIG. 9 and sequentially shows completion of a step of inversion of the apparatus, allowing fluids to flow into an absorption chamber.
Figure 11:
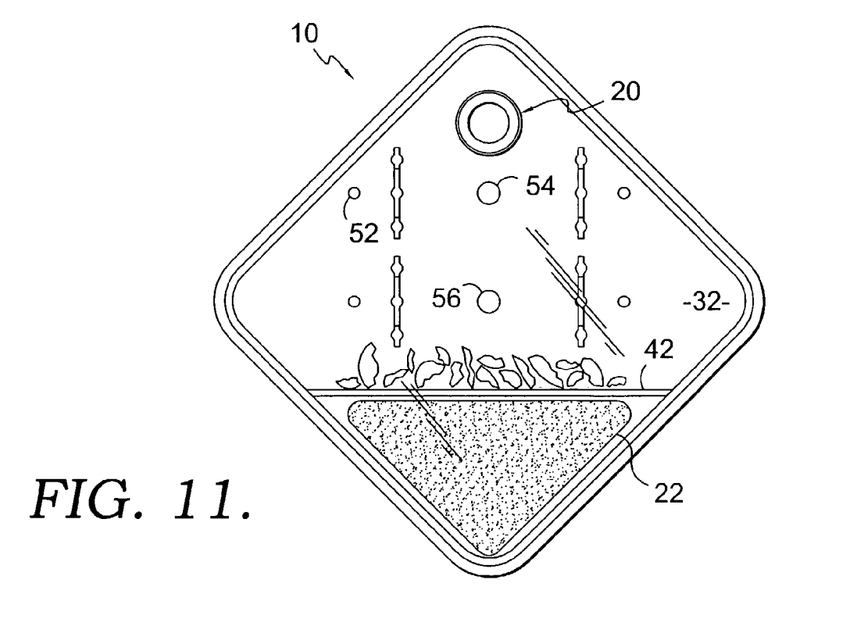
FIG. 11 is a top view similar to FIG. 10 and sequentially shows completion of a step of absorption of fluids by an absorbent material within the absorption chamber.

Thereafter, as best seen in FIG. 10, vessel 12 is inverted, allowing fluid pool 74 to flow between the inner surface of lid 26 and the upper edge of splash guard wall 42 and into absorption chamber 38. As best seen in FIGS. 11 and 12, absorbent material 22 absorbs fluid pool 74 at step 86 in order to reduce the amount of fluids from flowing freely between ampule chamber 38 and absorption chamber 40. Further, the weight of the absorbing pad may be predetermined so that the absorbent pad may be weighed after the drug test has been performed to check the amount of the drug wastage inserted into the injection port.

The present invention for drug testing overcomes or ameliorates the drawbacks and deficiencies in the prior art. Specifically, a hermetically sealed drug test vessel or chamber having frangible reagent containing vials or ampules contained therein and having or incorporating an ampule fracturing means adapted for fracturing the ampules contained within the test chamber without opening the chamber allows for the preservation of the results of a drug test. In addition, a portion of the apparatus may be transparent to allow for viewing of the test results without having to break the seal on the apparatus. Further, the fact that the one or more reagents are contained in an ampule within the sealed vessel eliminates the inconvenience of measuring each of the reagents and possibility of spilling or mis-measuring the amount of reagent that must be used to conduct the drug test.

While particular embodiments of the invention have been shown, it will be understood, of course, that the invention is not limited thereto, since modifications may be made by those skilled in the art, particularly in light of the foregoing teachings. Reasonable variation and modification are possible within the scope of the foregoing disclosure of the invention without departing from the spirit of the invention.

We claim:

1. A device for testing a test subject fluid for the presence of a drug, the device comprising:
  a vessel including an ampule chamber and an absorbing chamber,
  a splash guard wall disposed between the ampule chamber and the absorbing chamber, the splash guard wall for preventing the flow of the test subject fluid into the absorbing chamber before testing thereof, the splash guard wall also sufficiently limited in height to allow passage of fluids from the ampule chamber to the absorbing chamber after testing is complete,
  an absorbent material disposed within the absorbing chamber,
  a test subject injection port having an elastomeric membrane disposed in the wall of the ampule chamber adapted to allow injection of test subject fluid into the ampule chamber and further adapted to prohibit the escape of fluids from the vessel,
  at least one frangible ampule containing a first drug testing reagent mounted within the ampule chamber, the ampule chamber including brackets for cradling the at least one frangible ampule, and,
  an ampule fracturing lug for fracturing the frangible ampule, the ampule fracturing lug disposed on the wall of the ampule chamber of the vessel, the wall of the ampule chamber of the vessel being sufficiently flexible and the fracturing lug located and adapted such that manual deflection of the wall adjacent to the ampule fracturing lug will cause the ampule fracturing lug to break the frangible ampule thereby releasing the reagent contained therein, whereby test subject injection fluid injected through the injection port into the vessel may be tested by mixing with the reagent by breaking the frangible ampule and whereby the products of the mixing of the reagent and the test subject fluid may be spilled into the absorbing chamber for subsequent absorption by the absorbing material.

2. The device of claim 1, further comprising:
  a second drug testing reagent; and
  a second frangible ampule disposed within the ampule chamber, wherein the second ampule contains the second drug testing reagent, and,
  a second ampule fracturing lug in the wall of the ampule chamber for fracturing the second ampule.

* * * * *